ial Examiner—Richard C. Queisser

United States Patent [19]
Scott, Jr.

[11] 3,974,698
[45] Aug. 17, 1976

[54] MOLTEN METAL SAMPLER FOR ELECTROSLAG REFINING PROCESS

[75] Inventor: William W. Scott, Jr., Parkesburg, Pa.

[73] Assignee: Lukens Steel Company, Coatesville, Pa.

[22] Filed: Jan. 24, 1975

[21] Appl. No.: 544,011

[52] U.S. Cl............................. 73/425.6; 73/DIG. 9
[51] Int. Cl.².......................................... G01N 1/14
[58] Field of Search....................... 73/425.6, DIG. 9

[56] References Cited
UNITED STATES PATENTS

| 3,255,634 | 6/1966 | Cavalier | 73/DIG. 9 |
| 3,309,928 | 3/1967 | Cavalier | 73/DIG. 9 |
| 3,490,289 | 1/1970 | Mangin | 73/DIG. 9 |

FOREIGN PATENTS OR APPLICATIONS

| 249,417 | 9/1966 | Austria | 73/DIG. 9 |
| 86,587 | 1/1966 | France | 73/DIG. 9 |

Primary Examiner—Richard C. Queisser
Assistant Examiner—Joseph W. Roskos
Attorney, Agent, or Firm—Mason, Mason & Albright

[57] ABSTRACT

A molten metal vacuum-type sampler for taking samples of molten metal from the mold used in an electroslag refining process while opposite voltages are applied across the electrode and the mold, the sampler being a box-shaped hollow body with a silica tube extending downwardly therefrom to be inserted through the slag cover into the molten metal for a few seconds to draw a metal sample into the hollow space of the sampler. The sampler has two insulation boards on opposite sides overlapping the sides to prevent an electrically conductive contact of the sampler with the nearby surfaces of the mold and the electrode. An insulated pipe attached to the top of the sampler forms a handle in its upper aspect and connects conduits and a valve optionally to an argon gas source or a vacuum reservoir. Argon is discharged into the supporting pipe, through the sampler and the silica tube when the tube is inserted in the slag and into the molten metal at which time the vacuum reservoir is placed in communication with the sampler vice the argon source for a predetermined short period (about 5 seconds) and metal is drawn through the silica tube into the sampler, the amount of metal being predetermined by the size of the vacuum reservoir and the degree of vacuum therein. The length of time to obtain the desired sample is governed by a restriction in the conduit to the vacuum reservoir. The interior of the sampler has its sides formed in a converging relationship to facilitate removal of the metal sample.

22 Claims, 11 Drawing Figures

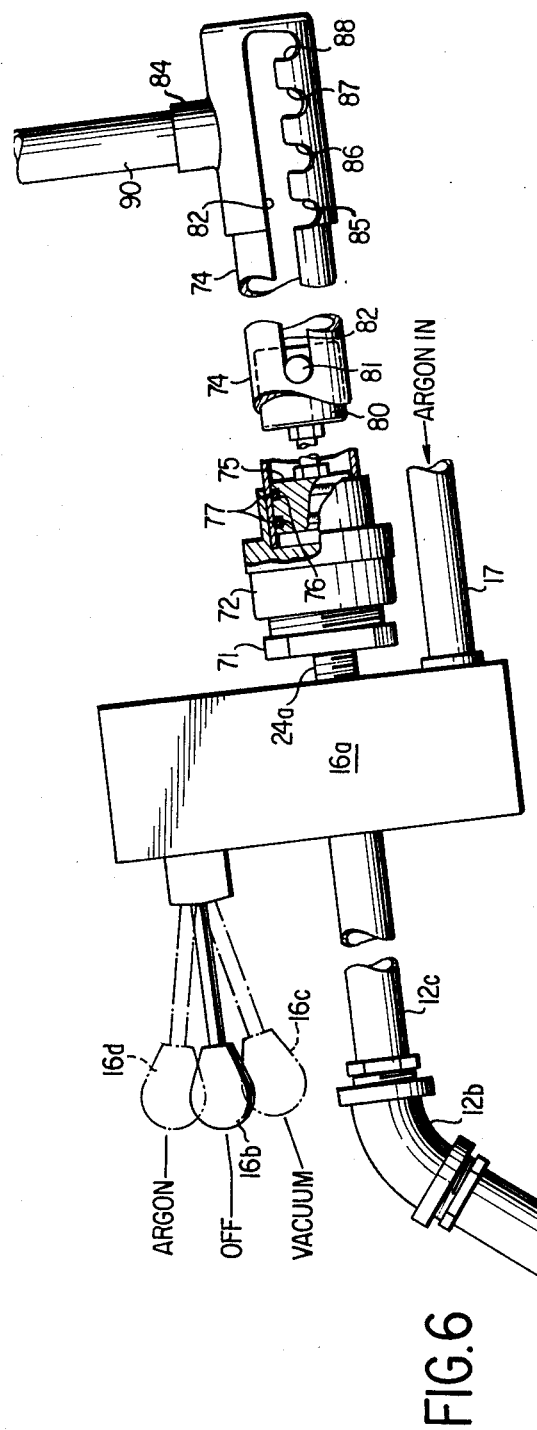
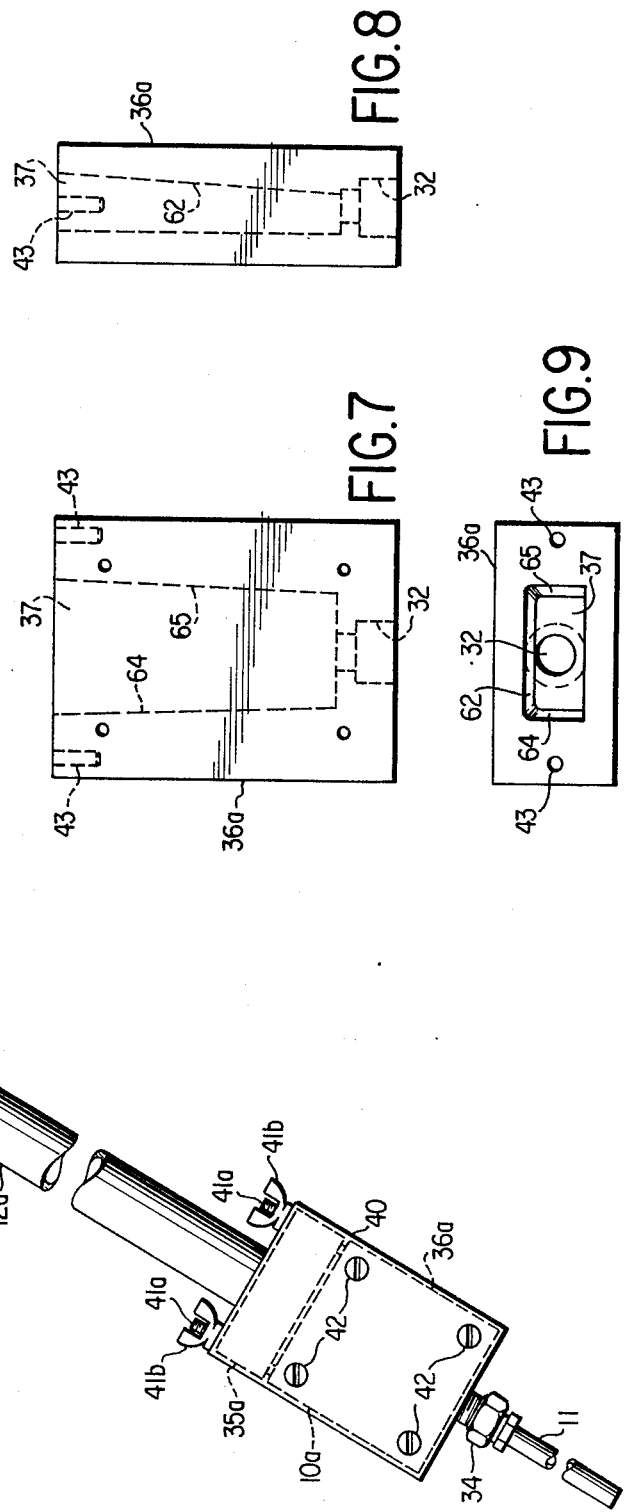

MOLTEN METAL SAMPLER FOR ELECTROSLAG REFINING PROCESS

BACKGROUND OF THE INVENTION

Obtaining a metal sample in the electroslag refining process with the electrical power applied is difficult because the sampler must be lowered between two relatively close (about 2 to 4 inches) flat surfaces which are oppositely charged and thus the electrical hazard is aggravated by the tight geometrical situation. In addition, the slag contains a substantial amount of calcium fluoride ($CaF_2$) which is highly corrosive and has the capacity of rapidly dissolving almost any standard steel making refractory. Still further, sampling is in any event difficult when metal is covered by slag and this difficulty is accentuated in the electroslag refining process due to the agitation of the slag and the underlying liquid metal. Thus, for the electroslag refining process, a need exists for samplers which will not present an electrical hazard to the operator or adversely affect the process, which are constructed of materials which will stand up when exposed to the highly corrosive slag and which can be utilized under conditions of the process wherein agitation is occurring in the underlying molten metal and in the slag.

SUMMARY OF THE INVENTION

The instant invention relates to a liquid metal sampler to be used in electroslag refining process. In particular, the invention is directed to such a sampler which may be employed with the electrical power applied and without interrupting or disrupting the ongoing process.

The solution to the problems set forth under the background of the invention has been met by providing a sample block or mold which is effectively electrically insulated for the sampling process through utilization of a pair of insulating boards on either side of the mold overlapping its sides whereby contacts between the metal mold and the surfaces of the mold or the electrode or both are fully prevented. The gear for manipulating the sample block comprises a metal pipe which is insulated on its exterior. Further, the conduit to be inserted into the molten metal is a silica tube having good electrical insulation characteristics. Thus, the possibilities of electrical hazard have been substantially eliminated as a practical matter. The silica tube is also capabe of withstanding thermal shock and at the same time the corrosive effects of the calcium fluoride base slag for the 4 to 5 seconds necessary to obtain a sample. When the silica tube is lowered through the slag, an inert gas, argon, is metered through the pipe and sample block and discharged from the tube to eliminate any slag entrainment. However, when the tube is in the desired position inserted in the molten metal which underlies the slag, the conduits which lead to the tube through the handle and the sample block are disconnected from the argon source and connected to a vacuum reservoir whereby in a predetermined length of time, molten metal is drawn through the silica tube into the sampler — filling an interior hollow space. The sampler is then withdrawn and the sample block can be readily opened to facilitate removal of the sample for the desired analysis.

The primary object of the instant invention is to present a liquid metal sampler for use in electroslag refining process which performs its functions efficiently, effectively and safely thus overcoming the problems entailed in such a process as outlined above. However, other objectives, adaptabilities and capabilities of the invention will be recognized by those skilled in the art as the description progresses, reference being had to the accompanying drawings.

BRIEF DESCRIPTION OF THE DRAWINGS

FIG. 6 shows in the side elevation and partial section a further embodiment of the invention;

FIGS. 7, 8 and 9 constitute front and side elevations and a top view of the body portion of the sample block of the further embodiment;

DESCRIPTION OF THE PREFERRED EMBODIMENT

Figure 1:
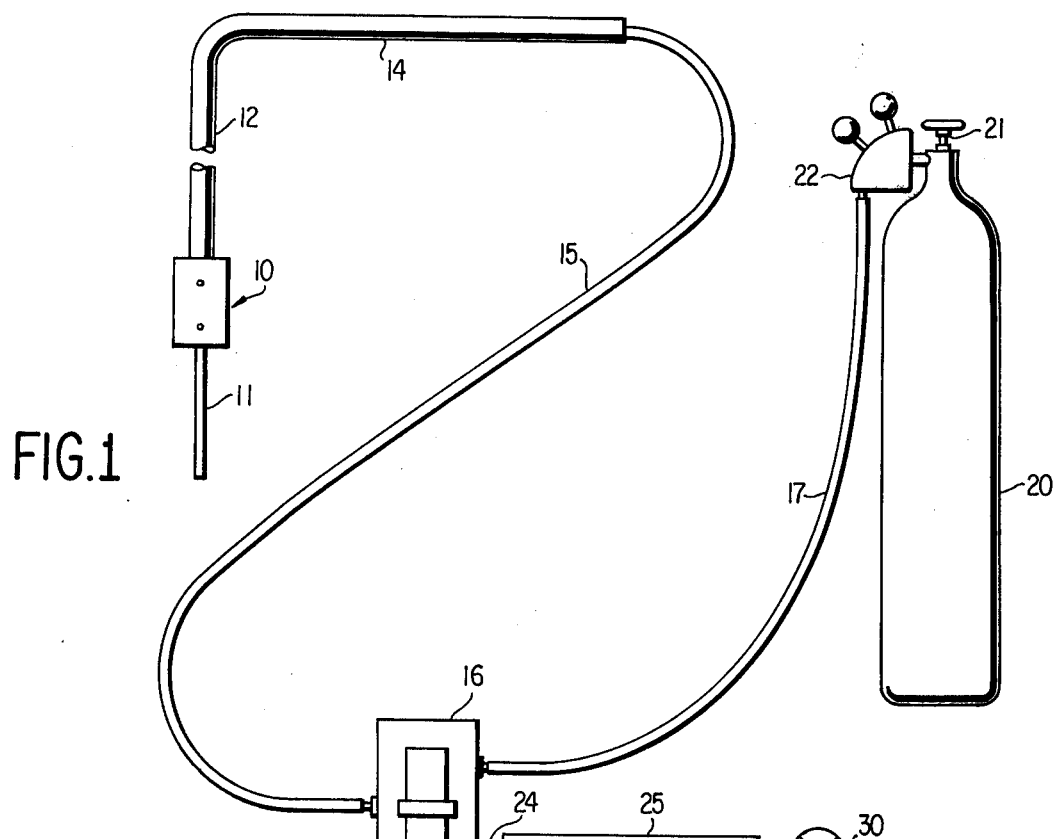
FIG. 1 is a diagrammatic representation of the required equipment for a first embodiment of the sampler in accordance with the invention.

Referring now to FIG. 1, a sample block 10 receives at its lower end a silica tube 11 and is supported at its upper end by an insulated pipe 12 which includes a bent over portion 14 serving as a handle. Pipe 12 comprises a first conduit from the sample block 10 which connects at its end away from block 10 to a second conduit 15 composed of a flexible material leading to a two-way foot-valve 16 which has one connection via a third conduit 17 to a pressure vessel 20 which contains argon gas under pressure and includes a stop valve 21 and a flow regulator 22 into which conduit 17 connects. A further connection from valve 16 comprises a fourth conduit 24 which connects to a vacuum reservoir 25 which, in turn, is connected to a motor driven vacuum pump 26 via a fifth conduit 27 containing a stop valve 30.

Figure 3:
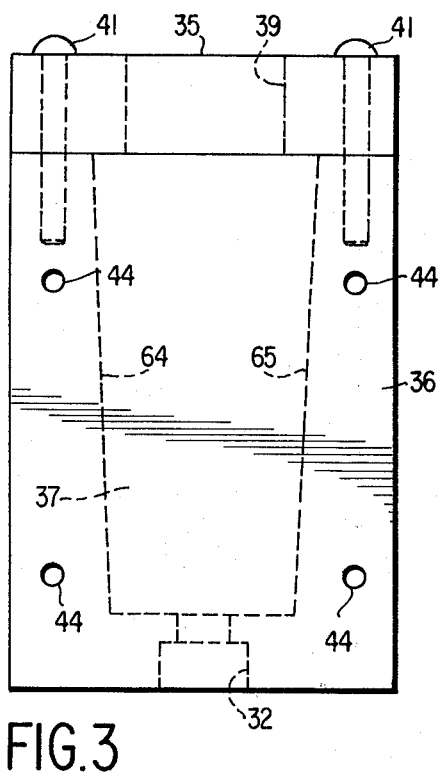
FIG. 3 is a front elevational view of a sample block in accordance with the invention with the insulating boards removed therefrom.
Figure 4:
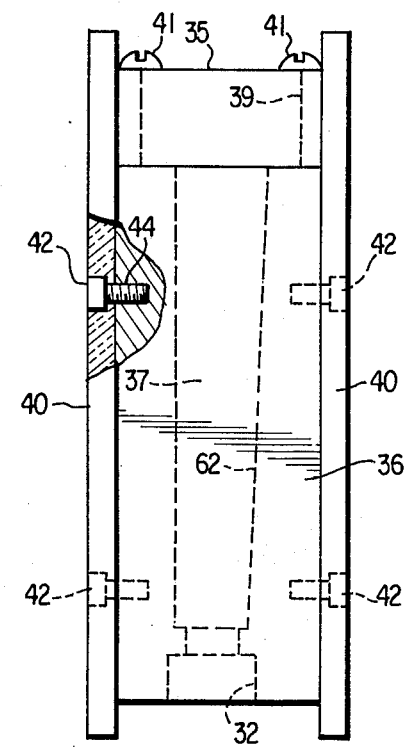
FIG. 4 is a side elevational view of the sample block shown in FIG. 3 with, however, the insulating boards applied.
Figure 5:
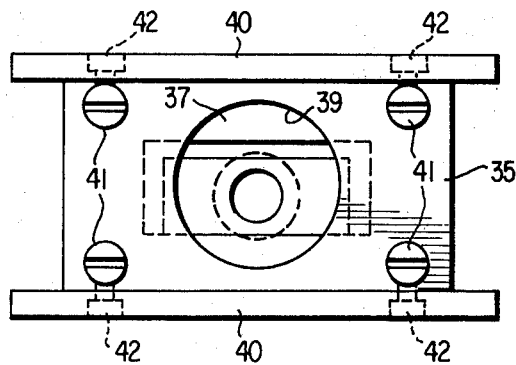
FIG. 5 is a top view of the sample block shown in FIGS. 3 and 4 with the insulating boards applied thereto.
Figure 10:
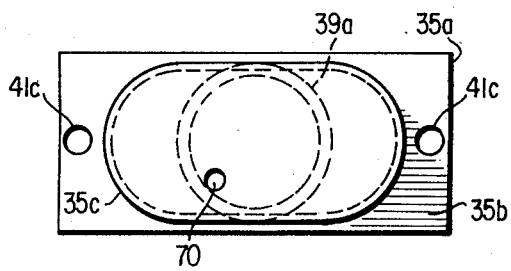
FIG. 10 is a bottom view of the top portion of the sample block of the further embodiment.
Figure 11:
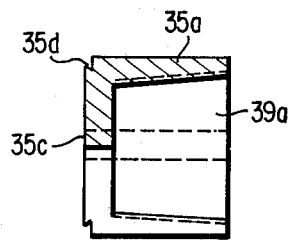
FIG. 11 is a side view in partial section of the top portion shown in FIG. 10.

Before sampling, a disposable rubber O-ring 31 is fitted onto tube 11 and tube 11 is placed in the threaded opening 32 at the bottom of sample block 10. A retaining bushing 34 is fitted over tube 11 and threaded into the opening 32 thus compressing O-ring 31, holding tube 11 and providing an airtight seal. The sample block 10 comprising a top portion 35, a body portion 36 with an interior space 37 which connects with the bottom opening 32. Each wider side of body portion 36 has secured thereto an insulating board 40. A small portion of vacuum grease is placed on the mating surfaces of the top portion 35 and body portion 36 which are then assembled to provide an airtight seal of space 37 within the block 10. The sealing of the block 10 is accomplished by the tightening of the threaded screws 41 as shown in FIGS. 3 – 5, pipe 12 having already been threadably received in an opening 39 of the top portion 35 which communicates with space 37. Insulating boards 40 are connected to body portion 36 by means of bolts 42 received in openings 44 provided in body portion 36. It will be noted that insulating boards 40 overlap the edges of sample block 10 on all sides.

Figure 2:
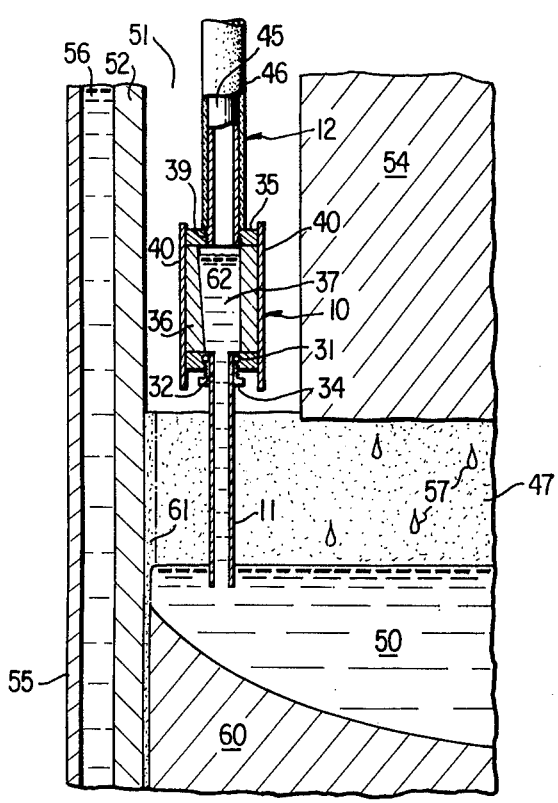
FIG. 2 illustrates a molten metal sample being drawn from electroslag refining melt.

With sample block 10 ready for use with tube 11 inserted therein as shown in FIG. 2 and also receiving pipe 12 which consists of a steel ¾ inch pipe 45 covered with asbestos insulation 46, argon is connected by activating foot valve 16 so that it flows via the third conduit 17, valve 16, second conduit 15, pipe 12, through sample block 10 and finally tube 11. The argon pressure from vessel 20 is regulated by regulator 22 so that slag 47 will not be received therein when the tube 11 is inserted through slag 47 and into the metal liquid 50 as illustrated in FIG. 2.

As shown in FIG. 2, the space 51 between the mold wall 52 and the metal electrode 54 is not great, perhaps 2 to 4 inches. Both electrode 54 and mold wall 52 have electrical current applied thereto and opposite voltages to present a voltage differential from between about 40 and 80 volts. Mold wall 52 has spaced therefrom a water jacket 55, cooling water 56 being provided in the space between wall 52 and jacket 55.

In the electroslag refining process, due to the heat generated by electrical current passing through slag 47, the end of electrode 54 is melted and drops of molten metal 57 fall through slag 47 into a molten metal pool 50 which solidifies in the bottom portion 60 of the mold and due to the cooling effect of water 56 a slag skin 61 forms.

In operation, the operator, by means of handle 14, quickly inserts the block 10 so that it is just a short distance above the top of slag 47 as shown in FIG. 2. As indicated above, there is during this period of time a flow of an inert gas, argon, through pipe 12, block 10 and tube 11. However, as soon as the sampler is in the position shown in FIG. 2, the argon flow is quickly terminated and the vacuum reservoir 25 is connected via the fourth conduit 24 and valve 16 to the second conduit 15 and thus to the pipe 12, block 10 and silica tube 11 inserted the liquid metal to. The size of vacuum reservoir 25 and the interior diameter of the tubing 15 from handle 14 to foot valve 16 are carefully selected so that with the end of tube 11 subjected to the vacuum in vacuum reservoir 25, as described, in a predetermined period of time, preferably about five seconds, the desired amount of molten metal is drawn up into the interior 37 of sample block 10 which is then raised out of the mold. Screws 41 are next loosened and the sample is removed for the deisred analysis. In this connection, it will be noted that the interior 37 of body portion 36 includes three sides 62, 64 and 65 which converge in a downward direction thus permitting the sample to be readily disengaged from the sample block 10 by tapping same through opening 32.

Referring now to FIGS. 6 – 11, a silica tube 11 composed of fused quartz is received by bushing 34 with a seal comprising an O-ring 31(not shown in FIG. 6) in a manner similar to that described in reference to the first embodiment. A sample block 10a is provided with insulating boards 40 which are secured to its body portion 36a by means of bolts 42 on both of the wider sides of the sampler block 10a. The body portion 36a is substantially identical to body portion 36 of the previously described embodiment except that it is provided with only two openings 43 which receiving studs 41a upon which are received wing nuts 41b to secure the top portion 35a to body portion 36a. Otherwise similar reference numerals have been applied to the body portion 36a as applied to body portion 36. With reference to the top portion 35a, a bore 39a is threaded to receive the pipe 12a, the bottom 35b of top portion 35a is solid except for a ⅛ opening 70 and the holes 41c through which extend studs 41a. Bottom 35b includes an oval-shaped plateau 35c which extends outwardly a short distance from the remainder of bottom 35b and its sides 35d are disposed at a 60° angle to the remaining part of bottom 35b. The purpose of this arrangement is to make provision about plateau 45c, adjacent to and contacting the sides 35d for receipt of an O-ring to provide a sealing engagement of top portion 35a with body portion 36a of sample block 10a.

Pipe 12a is preferably from about 40 to 60 inches long and is provided with a wrapping of teflon tape in three layers to constitute a high temperature and electrical insulation. The upper end of pipe 12a is received by an elbow 12b which on its other end receives a nipple. Opposite the elbow 12b, nipple 12c connects with a three-way valve 16a controlled by a hand lever 16b which has three positions, the "off" position as shown in FIG. 6, the vacuum connection position 16c shown in dot-dash lines, for connection to the vacuum reservoir, and an argon connection 16b, also shown in dot-dash lines, for connection to an argon source such as pressure vessel 20 shown in FIG. 1. The argon is provided via a conduit 17 which connects with a regulator means 22 of a pressure vessel 20 as shown in FIG. 1.

A nipple 24a, connected into the three-way valve 16a, has in its interior a 1/16th inch orifice welded therein. Nipple 24a is threadably received by a bushing 71 which, in turn, has threaded thereon an adapter member 72. Extending from the other side of adapter member 72 and affixed thereto is a cylinder member 74. A piston 75 is received in cylinder member 74 which has cylindrical recesses 76 receiving a pair of O-rings 77 to provide a sealing engagement between piston 75 and cylinder member 74.

Piston member 75 is connected to a guide block 80 by means of a threaded connecting rod 81. Extending normally from and rigidly connected to a guide block 80 is a handle rod 81 which, as shown in FIG. 6, is received at the left or forward end of a slot 82 which is provided in the cylinder member 74 and also in a tee member 84 which fits on the after end of cylinder member 74. Further, tee member 84 together with cylinder member 74 also define a plurality (four) further slots or notches 85, 86, 87 and 88, the center-line of each forming an 80° angle with the center-line of slot 82. Each notch 85, 86, 87 and 88 is adapted to receive the handle rod 81 to secure piston 75 together with the guide block 80 in a selected fixed position relative to the cylinder member 74. The purpose of the pipe member 90 which is received in tee member 84 is to function as a shoulder rest for the operator who, upon pulling the handle rod 81 to the right as seen in FIG. 6, creates a vacuum in the space defined by cylinder member 74 forward of piston 75, adapter 72, bushing 71, to the valve cutoff of the three-way valve 16a. The degree of vacuum so created depends on the notch 85, 86, 87 or 88 which is selected for receiving the handle rod 81 after it has been pulled back by the operator. Thus it will be appreciated that in lieu of the vacuum pump 26, shown in FIG. 1 of the previous embodiment, a vacuum reservoir is created manually in the instant embodiment with the particular degree of vacuum, or the effective reservoir size, being determined by the displacement of the piston 75.

In operation, the individual taking the sample places pipe 12 between electrode 54 and mold wall 52 and turns the hand lever 16b, controlling three-way valve 16a, so that argon flows from conduit 17 into valve 16a, nipple 12c, elbow 12b, pipe 12a, sample block 10a, and finally through and is discharged from tube 11 prior to being inserted into slag 47. He then positions tube 11 so that it extends through slag 47 and into molten metal 50 as shown in FIG. 2. With the sampler properly positioned, the operator immediately moves the hand lever 16b to the vacuum position 16c and the piston 75 already having been pulled back with the handle rod received by selected 85, 86 87 or 88, a vacuum reserve exists forward piston of 75 which is communicated via valve 16a, nipple 12c, elbow 12b, pipe 12a, sample block 10a and tube 11 to draw into the interior space 37 of sample block 10a a predetermined amount of molten metal. The molten metal is prevented from surging by the orifice in the nipple 24a which, as before, also governs the time of the operation preferably 4 to 5 seconds. In addition, the offset orifice 70 in the plateau 35c is operative to prevent metal or metal drops surging into the pipe 12a and bore 39a.

When the metal has been obtained, the sampler is immediately withdrawn from the mold and the top portion 35a is quickly disconnected by removing wing nuts 41b. Tube 11 together with O-ring 31, which are expendable, are next removed and the sample is tapped by a hammer or the like through opening 32 to loosen the metal sample from the interior space 37. It is then utilized for analysis of the metal being produced in the electroslag refinery process.

The ratio of the effective volume of the vacuum reservoir 25 in the first embodiment or the vacuum reservoir forward of the piston 75 in the second embodiment to the volume of the sampler below the three-way valve 16a has been calculated to have a theoretical value of between 0.4 and 0.6 depending upon the depth of the slag 47 and thus the length of the silica tube 11. However, the actual value of this ratio based on experience ranges from 0.65 and 0.8. Utilizing this latter value, it will be appreciated that the samplers shown in both embodiments are designed to span such range depending on the depth of the slag 74. In other words, the vacuum reservoirs in both samplers are selectively adjustable depending upon the slag depth.

From the foregoing, it will be understood that four parameters require careful selection: (1) the length of silica tubing; (2) the effective size of the vacuum reservoir 25 or that forward piston 77 in the second embodiment; (3) the diameter tubing or other restriction in the conduit so that entry of gases from the sample block 10 is slowed with the result that the sample is withdrawn from the liquid pool 50 comparatively slowly; and (4) the argon pressure should be carefully adjusted by means of the regulator valve 22 depending on the quantity of the slag 47. However, one skilled in the art with this disclosure before him should be able to make these selections with little difficulty depending on the size and type of electroslag refining process to which the samplers in accordance with the invention are to be applied. In this connection, although the disclosure herein is directed to the preferred embodiments of the invention, it is to be understood that it is capable of other adaptations and modifications within the scope of the appended claims.

Having thus described my invention, what I claim as new and desire to secure by Letters Patent of the United States is:

1. A liquid metal vacuum sampler for sampling metal produced by the electroslag refining remelting process during the process while voltage is applied to the consumable electrode and to the mold whereby the sampler draws metal through the slag between the electrode and mold, the dampler comprising a first conduit which is insulated, a three-way valve, a second conduit interconnecting one end of said first conduit and said three-way valve, third and fourth conduits connected to said three-way valve, a source of inert gas under pressure higher than the ambient atmospheric pressure, said source having a fluid passageway to said three-way valve via said third conduit which is connected to said inert gas source, a vacuum source connected to said fourth conduit whereby fluid entering said fourth conduit and said three-way valve is drawn to said vacuum source through said fourth conduit, a hollow body for receiving a sample connected to the other end of said first conduit, said body being relatively enlarged and provided with sufficient insulation to preclude accidental short circuiting of said electrode and said mold, said body including a removable plate means for removing the sample metal therefrom a tube composed entirely of a material having a high dielectric constant connected to said body, said tube being of sufficient length to extend through the slag of an electroslag remelting process and into the liquid metal, whereby when said second conduit is connected by said three-way valve to said inert gas source, an inert gas flows from said inert gas source via said first, second and third conduits into said body and is discharged through said tube and when said three-way valve conects said second conduit to said vacuum source and said tube extends into said liquid metal, a sample of said metal is drawn into said body by said vacuum via said first, second and fourth conduit through said tube.

2. A sampler in accordance with claim 1, wherein said inert gas is argon.

3. A sampler in accordance with claim 1, wherein said tube is composed of silica.

4. A sampler in accordance with claim 1, wherein said body is box-shaped and said insulation comprises insulation boards applied to two opposite sides of said body, said insulation boards completely covering said sides in an overlapping relationship.

5. A sampler in accordance with claim 4, wherein said body comprises a top, a side plate comprising said removable plate means, and body portion defining the interior hollow space of said body on at least three sides.

6. A sampler in accordance with claim 1, wherein said fourth conduit is restricted whereby the desired sample of metal is drawn into said body in a predetermined period of time.

7. A sampler in accordance with claim 6, wherein said restriction of said fourth conduit is such that said predetermined length of time is three to ten seconds.

8. A sampler in accordance with claim 7, wherein said predetermined length of time is about five seconds.

9. A sampler in accordance with claim 1, wherein said first conduit comprises a metal pipe surrounded by insulation.

10. A sampler in accordance with claim 9, wherein said first conduit includes handle means in its upper aspect.

11. A sampler in accordance with claim 1, wherein said inert gas source comprises a pressure vessel containing said inert gas and inert gas flow regulating means connected to the discharge provided for said vessel to said third conduit.

12. A sampler in accordance with claim 1, wherein said vacuum source comprises a vacuum reservoir connected to a vacuum pump.

13. A sampler in accordance with claim 12, wherein the size of said vacuum reservoir is such as to cause the desired amount of metal to be drawn into said body.

14. A sampler in accordance with claim 1, wherein said three-way valve includes foot control means.

15. A sampler in accordance with claim 1, wherein said first and second conduits are rigidly connected together.

16. A sampler in accordance with claim 1, wherein said second conduit is nonintegral with said first conduit.

17. A sampler in accordance with claim 16, wherein said second conduit comprises a flexible member.

18. A sampler in accordance with claim 1, wherein said vacuum source comprises a vacuum reservoir.

19. A sampler in accordance with claim 18, wherein said vacuum reservoir is selectively adjustable.

20. A sampler in accordance with claim 18, wherein said vacuum reservoir is created by piston and cylinder members connected directly on the sampler.

21. A sampler in accordance with claim 20, wherein said vacuum reservoir is created by manually moving said piston relative to said cylinder.

22. A sampler in accordance with claim 18, wherein the ratio of the effective vacuum reserve prior to said three-way valve to the volume of the sampler below said three-way valve ranges between about 0.65 and 0.8.

* * * * *